United States Patent
Fishbaugh

(10) Patent No.: US 7,052,130 B2
(45) Date of Patent: May 30, 2006

(54) PROTECTIVE EYEWEAR

(75) Inventor: Brenda B. Fishbaugh, Fort Wayne, IN (US)

(73) Assignee: EP Acquisition, Inc., Fort Wayne, IN (US)

( * ) Notice: Subject to any disclaimer, the term of this patent is extended or adjusted under 35 U.S.C. 154(b) by 0 days.

(21) Appl. No.: 11/026,140

(22) Filed: Dec. 30, 2004

(65) Prior Publication Data

US 2005/0140923 A1    Jun. 30, 2005

Related U.S. Application Data

(60) Provisional application No. 60/533,183, filed on Dec. 30, 2003.

(51) Int. Cl.
  *G02C 7/10*    (2006.01)

(52) U.S. Cl. .................. 351/44; 351/41; 2/12; 2/15

(58) Field of Classification Search .............. 351/41, 351/44; 2/12, 15
See application file for complete search history.

(56) References Cited

U.S. PATENT DOCUMENTS

| | | | |
|---|---|---|---|
| 915,738 A | 3/1909 | Burdick | 604/308 |
| 1,161,321 A | 11/1915 | Lush | 604/308 |
| 2,165,668 A | 7/1939 | Vaccaro | 2/15 |
| 2,283,752 A | 5/1942 | Gonsett | 2/15 |
| 2,341,673 A | 2/1944 | Walker | 52/786.13 |
| 2,527,947 A | 10/1950 | Loos | 604/294 |
| 2,572,638 A | 10/1951 | Loos | 128/858 |
| 2,709,256 A | 5/1955 | Baratelli | 2/447 |
| 2,759,394 A | 8/1956 | Evans | 128/858 |
| 3,068,863 A | 12/1962 | Bowman | 128/858 |
| 3,092,103 A | 6/1963 | Mower | 128/858 |
| 3,269,267 A | 8/1966 | Collins | 351/44 |
| 3,300,786 A | 1/1967 | Rosenvold et al. | 2/15 |
| 3,619,815 A | 11/1971 | Towner, Jr. | 2/12 |
| 3,756,692 A | 9/1973 | Scott | 359/241 |
| 3,758,202 A | 9/1973 | Chunga, Sr. | 351/41 |
| 3,780,379 A | 12/1973 | Kampman | 2/15 |
| 4,024,405 A | 5/1977 | Szot | 250/516.1 |
| 4,122,847 A | 10/1978 | Craig | 128/858 |
| 4,162,542 A | 7/1979 | Frank | 2/15 |
| 4,411,263 A | 10/1983 | Cook | 128/858 |
| 4,567,122 A | 1/1986 | Baldry et al. | 430/4 |
| 4,599,746 A | 7/1986 | Stoner | 2/15 |
| 4,642,816 A | 2/1987 | Miller | 2/15 |
| 4,682,371 A | 7/1987 | Heltman | 2/15 |
| 4,701,962 A | 10/1987 | Simon | 2/15 |
| 4,793,002 A | 12/1988 | Simon | 2/15 |
| 5,263,200 A * | 11/1993 | Miller | 2/15 |
| 5,970,515 A | 10/1999 | Fishbaugh | 2/15 |

* cited by examiner

*Primary Examiner*—Huy K. Mai
(74) *Attorney, Agent, or Firm*—Barnes & Thornburg LLP

(57) ABSTRACT

An eye protector includes a UV protective film and has adhesive located at the ends of the major axis of the film. The film is sufficiently flexible that it can be shaped into a cane with an oblong base, whereby when the device is applied to a user's eye with its major axis aligned with the major axis of the eye, the adhesive is positioned such that it holds the device to the user's eye at opposite edges of the eye keeping the adhesive from interfering with the user's eyelid, which is particularly troublesome for women using eyeshadow. Methods for manufacturing and merchandising the eye protector are also disclosed.

40 Claims, 2 Drawing Sheets

PROTECTIVE EYEWEAR

This application claims priority to and the benefit of U.S. Provisional Patent Application Ser. No. 60/533,183, filed Dec. 30, 2003, the disclosure of which is now incorporated herein by reference.

BACKGROUND OF THE INVENTION

This invention relates to protective eyewear, or more particularly disposable protective eyewear.

Field of the Invention

Intense visible light or light of shorter wavelengths, i.e., between about 200 and about 400 nanometers (ultraviolet radiation), possesses a significant risk of injury to the human eye. This is true regardless of whether the light is from a natural or artificial light source. While the ultraviolet (UV) radiation component of sunlight can damage the eyes without proper protection, the majority of cases of UV radiation eye damage arise from the use, or more particularly the misuse, of artificial sunlamp products, for example, tanning beds and the like. In response to this danger, regulations have been promulgated to specify safety standards for the manufacturing and use of UV emitting products. One U.S. federal regulation, 21 C.F.R. §1040.20, now incorporated herein by reference, requires that protective eyewear be provided and used with all UV emitting lamps. To comply with these regulations, some lamp manufacturers and/or tanning salon proprietors have been supplying customers with reusable goggle-type protective eyewear. However, reusable protective eyewear presents certain sanitary problems as it can serve as a means for spreading communicable eye diseases of both microbial and viral origin. Because of this fact, many users of UV light emitting products, especially those in commercial settings, refuse to use the protective eyewear.

Another regulation pertinent to personal eye protectors is European Standard EN 170:2002, entitled Personal Eye Protection—Ultraviolet Filters, Transmittance requirements and recommended use, now incorporated herein by reference. EN 170 has the status of a national standard in at least Austria, Belgium, Czech Republic, Denmark, Finland, France, Germany, Greece, Ireland, Italy, Luxembourg, Malta, Netherlands, Norway, Portugal, Spain, Sweden, Switzerland and the United Kingdom. The EN 170 requirements for eye protectors used in conjunction with high-pressure mercury lamps and metal halide lamps such as sun lamps for solaria are as follows: The maximum spectral transmittance ($\tau(\lambda)$) in the ultraviolet is 0.0003% in the range 210–313 nm, is 2% in the range 313–365 nm, and is less than the luminous transmittance ($\tau$hd v) in the range 365–405 nm. The luminous transmittance must be between a minimum of 8.5% and a maximum of 17.8%.

The availability of a disposable, adjustable, and inexpensive eye protection for use with UV emitting devices, as well as for use in other circumstances requiring temporary protection of the eye from potential eye irritants, meets important public health and safety needs. Not only do such devices promote the use of appropriate eye protection at home and in the increasingly popular tanning salons, but it helps to minimize the spread of disease possibly associated with reusable protective eyewear. Commonly owned U.S. Pat. Nos. 4,739,002 (the "'002 patent") and 4,701,962 (the "'962 patent") disclose such disposable protective eyewear in which a conical eye protector is formed by overlapping and adhering portions of film members. The film members contain ultraviolet absorbing compounds, yet they allow sufficient visible light to pass through to enable the user to "see" while wearing the eyewear.

In the '962 patent, the film member is either circular or oval. The circular version includes a radial slit or scission line, and a band of adhesive around the perimeter of the disc. A person overlaps the edges at the slit, relying on the adhesive to hold the film in a conical configuration. The perimeter band of adhesive then adheres the cone-shaped film over the user's eye.

A generally elliptical-shaped film is also disclosed in the '962 patent, which includes a radial slit on the minor axis of the ellipse. In this version, adhesive is positioned only at the top and bottom of the minor axis of the ellipse. As above, the user overlaps the edge portions of the film at the slit, and then uses the adhesive at the top and bottom of the minor axis to adhere the resulting elliptical/cone-shaped member to the user's eye at the top and bottom thereof.

Another commonly owned patent, U.S. Pat. No. 5,970,515 (the "'515 patent"), discloses a variation in which the film member has one elongated side which is generally "C"-shaped in configuration, and an opposite elongated side which is "W"-shaped. In this device, adhesive is located along the elongated generally C-shaped edge, and within the "W" portions. The elliptical cone is formed by overlapping the projecting portions of the "W," and the exposed adhesive at the W and along the elongated C-shaped edge is used to adhere the device at the top and bottom of a user's eye. The CW-shaped film does not have a slit or scission line.

The disclosures of the '002 patent, the '962 patent and the '515 patent are now incorporated herein by reference.

SUMMARY OF THE INVENTION

The present invention may comprise one or more of the features set out in the co-pended claims or the following features or combinations thereof. The disposable eye protector of the present invention is a UV protective film which is oblong in configuration, and has adhesive located only on at least one of the ends of the major axis of the film, the film being sufficiently flexible that it can be shaped into a cone with an oblong base, whereby when the device is applied to a user's eye with its major axis generally aligned with the major axis of the eye, the adhesive is positioned such that it holds the device to the user's eye at the opposite ends of the eye, rather than along the top and bottom of the eye. This keeps the adhesive from interfering with the user's lashes, which is particularly troublesome for women using eyeshadow. The disclosed disposable eye protector may meet at least some of the transmittance requirements set forth in pertinent local, state, and federal rules, regulations, and laws. For example, the disclosed eyewear may meet at least some of the transmittance requirements set forth in EN 170:2002. Prior to forming the oblong conical configuration, the film may have an oblong shape having an elongated C-shaped portion and an opposing W-shaped portion such that it represents an elongated heart. By overlapping the separated portions of the "W" or heart, an asymmetrical cone may be formed. The disposable eyewear may provide the user with an indication of the proper formation of the oblong or asymmetrical cone by a recognizable shape formed by the separated portions or lobes when they are overlapped. For example, the overlapped lobes or portions may form a heart. The film may be monochromatic, or it may comprise more than one color. Illustratively, the lobes may be of a color different from the rest of the contiguous film.

In such a case, the recognizable shape will have a different color from the rest of the film.

A method for reducing the exposure of an eye to eye irritants and ultraviolet radiation is also provided. The method may comprise the steps of providing a film that can be shaped into a generally oblong conical configuration so that it can be fitted over a user's eye, the base of said oblong conical configuration having a major axis and shorter a minor axis, said film including an adhesive disposed on at least one side thereof, located generally at the ends of said major axis, said film being free of adhesive at the ends of said minor axis; forming said film into a generally oblong conical configuration; positioning said eye protector over the user's eye with its major axis corresponding to the major axis of the user's eye; and adhering said oblong conical configuration to at least one end of the user's eye rather than the top or the bottom of the user's eye.

A method of manufacturing disposable protective eyewear is also disclosed, the method comprising the steps of: providing a carrier web; adhering an adhesive to said carrier web, said adhesive being disposed along at least one edge and a center portion of said carrier web; positioning a layer a film material sufficiently flexible that it can be shaped into an oblong conical configuration so that it can be fitted over a user's eye; adhering said film material to said adhesive on said carrier; and cutting said film material to a first desired shape such that it can be further shaped into an oblong conical configuration, the base of said oblong conical configuration having a major axis and shorter a minor axis, said shape including a portion of said center portion and said at least one edge of said adhesive on said carrier.

Further disclosed is a method of merchandising disposable protective eyewear comprising the steps of: providing a plurality of protective eyewear film pieces, said film pieces disposed on a carrier; and providing at least one tanning decal disposed on said carrier alongside said disposable protective eyewear.

These and other features of the present invention will be further understood and appreciated by those skilled in the art by reference to the following specification, claims and appended drawings.

DESCRIPTION OF THE ILLUSTRATIVE EMBODIMENTS

Figure 1:
FIG. 1 is a perspective view illustrating one of the present eye protectors in use.

For the purposes of promoting an understanding of the principles of the invention, reference will now be made to a number of illustrative embodiments illustrated in the drawings and specific language will be used to describe the same.

With reference to FIG. 1 there is provided in accordance with this invention protective eyewear 2 of generally asymmetrical conical shape for fitting over the eye so that the eye protector's base is in contact with the soft tissue surrounding the eye. The eyewear of this invention is formed from a film segment 10 having a unique shape (the "elongated CW-shape") as shown best in FIGS. 2, 3 and 9.

Figure 2:
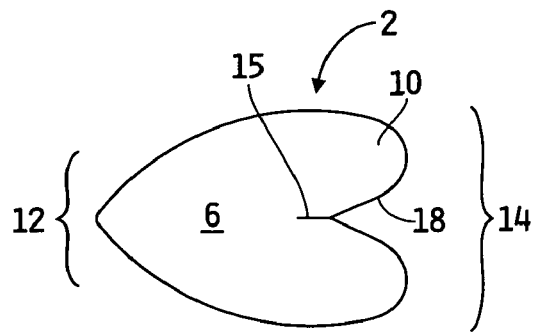
FIG. 2 is a top plan view of a film segment used to form one of the present eye protectors.

Protective eyewear patch 2 of the preferred embodiment is made of an ultraviolet (UV) reducing film material 10 cut into a generally oblong shape, having a longitudinal major axis and a lateral minor axis (FIG. 2). Film member 10 includes an eye proximal first side 4, an eye distal second side 6, a peripheral edge 18 and an adhesive 30 illustratively located only at the ends of the major axis of film 10. Film 10 is sufficiently flexible that it can be shaped into a cone with a generally oblong base 18, such that when the device is applied to a user's eye with its major axis aligned with the major axis of the eye (running generally from corner to corner of the eye), adhesive 30 is positioned such that it holds the device to the user's eye at the opposite ends of the eye, rather than along the top and bottom of the eye.

Figure 3:
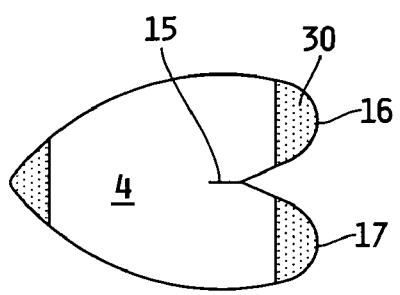
FIG. 3 is a bottom plan view of a film segment used to form one of the present eye protectors.
Figure 9:
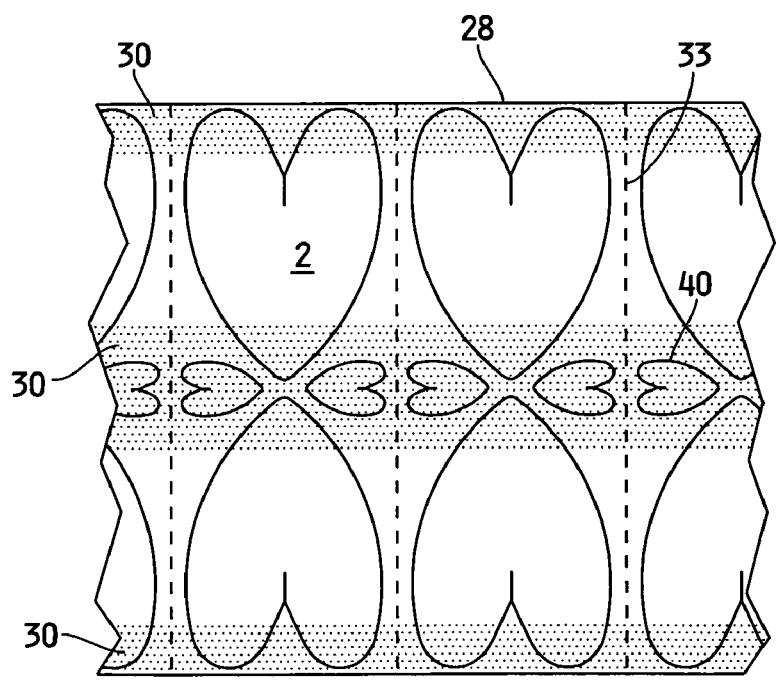
FIG. 9 is a top plan view of an illustrative carrier sheet during manufacturing having illustrative film segments used to form the present illustrative eye protectors.

More particularly, peripheral edge 18 of film material 10 is defined by a generally C-shaped portion 12 and an opposing generally W-shaped portion 14 (FIG. 2), located at opposite ends of the major or longitudinal axis of the film. Illustratively, the generally C-shaped portion 12 is elongated. As used herein, the terms C-shaped and W-shaped are to be understood and used in their broadest sense. That is to say that the letters "C" and "W," like any letters, can have a variety of different shapes and still be recognizable as "C's" and "W's." In general, the "C"-shaped portion is characterized by curved top and bottom legs, joined by a base, and the "W"-shaped portion is characterized by two halves comprising two joined generally "V"-shaped portions which may have pointed or rounded bases or lobes, which are separated from one another. In either case, the specific configurations of the letter "C" and the letter "W" may vary. What is particular to W-shaped end 14 is the formation of lobes, halves, tabs, projections or extending portions 16 and 17, whereby these lobes can be overlapped to form a conically shaped eyewear piece as will be explained. As best seen in FIGS. 2, 3 and 9, the CW-shaped film 10 illustratively forms a generally heart-shaped member prior to folding the lobes 16 and 17 of the "W"-shaped portion 14 to form the illustrative and generally conically shaped eye protector as will now be explained.

Opposing lobes 16 and 17 of the "W"-shaped portion define a separation in film 10 which begins generally at the end of the major or longitudinal axis of film 10. The separation created by lobes 16 and 17 of the "W"-shaped portion is continued by a slit or scission line 15 extending from the point at which the lobes generally meet, generally along said major axis. Thus, the lobes 16 and 17 are at the distal end of slit 15. Lobes 16 and 17 converge at slit 15 to form the W-shaped end 14 of eyewear or eye protector 2.

Figure 4:
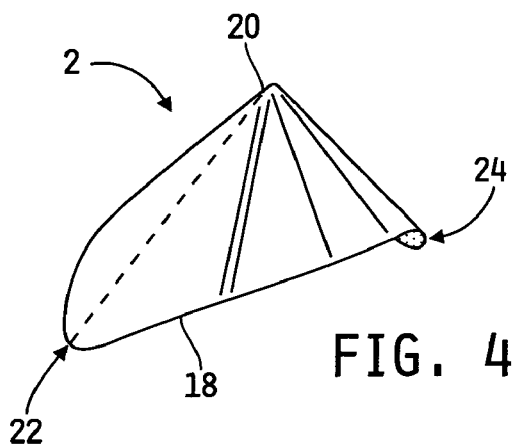
FIG. 4 is a perspective view of an illustrative asymmetric cone-shaped eye protector formed from the film segment depicted in FIG. 3.

Adhesive 30 illustratively is applied to the eye proximal first side of at least a portion of both lobes 16 and 17 of W-shaped portion 14 (FIG. 3). In use, the adhesive coated surface of either lobe, disposed on eye proximal first side 4, is positioned over the corresponding eye distal second side 6 of the opposite lobe and adhered, forming film member 10 into a conical shape with an apex 20 which is the improved eye protector 2 (FIG. 4). The formation of the conical shape is made easier by the addition of slit 15, which permits lobes 16 and 17 to be more easily folded over and onto one another. This is accomplished by allowing the edge of the slit of the lobe being moved, to fold under or on top of the corresponding lobe's slit edge.

Figure 6:
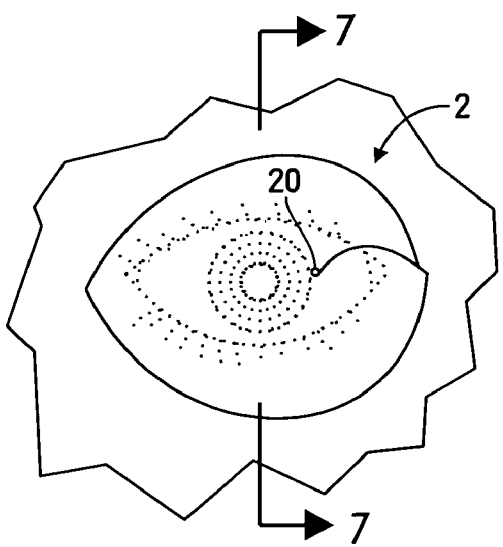
FIG. 6 is a top plan view of the illustrative eye protector of FIG. 4 positioned over a user's eye.

Slit 15 illustratively stops short of the center of the major axis, such that apex 20, which is formed at the proximal end of slit 15 when lobes 16 and 17 are overlapped, is disposed to one side of the center of the major axis, such that apex 20 generally is out of the direct line of sight of the user. The apex and overlapped portions create areas of high distortion and therefore, reduced visibility. By varying the length of slit 15, the location or positioning of apex 20 can be controlled. By positioning apex 20 to one side of the center of the major axis, the distorted area is positioned with the apex out of the "line of sight" of the user. This positioning tends to broaden the field of vision by decreasing the distortion of film member 10 in an area directly over the user's pupil and results in a significantly less obstructed field of view than that provided by prior art eye protectors (FIG. 6).

The height of the conical shape is also controlled by the length of slit 15. Slit 15 allows a person such as for example and without limitation a user to form a cone shape which is tall enough to accommodate a user's protruding eye, without having to extend the "W" separation further down the length of the major axis of the device. When slit 15 is lengthened, the conical height is reduced, wherein when slit 15 is shortened the height is increased. The height of the eyewear can thus be altered to allow the user relatively unrestricted eye movement which allows the user to blink or close the eye comfortably.

Figure 5:
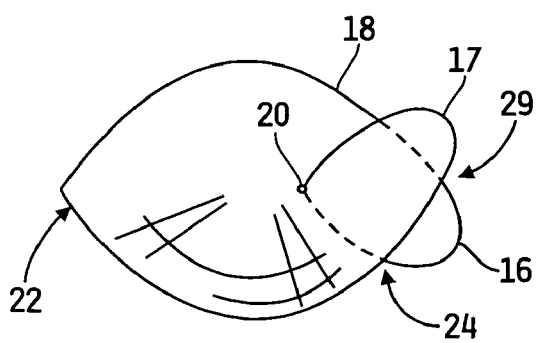
FIG. 5 is a top plan view of the illustrative eye protector of FIG. 4.

As described earlier, lobes 16 and 17 can take the form of various shapes and sizes and can be overlapped to form the conically shaped eyewear piece or eye protector. Additionally, by varying the position or amount of overlap of lobes 16 and 17, base 18 can be increased or decreased in size, thereby making improved eye protector 2 adjustable to accommodate specific users (FIGS. 4 and 5).

Opposite W-shaped end 14 is C-shaped end 12. C-shaped end 12, again, can take the form of various shapes and sizes and as used herein the C-shape is used to describe an illustrative embodiment only. For example, end 12 may be rounded or pointed. Illustratively, at least a portion of C-shaped end or portion 12 has adhesive 30. It will be appreciated that although the adhesive 30 could be provided on a portion of both lobes 16, 17 and a portion of C-shaped end 12 as has been described, it could also be provided on a portion of both lobes 16, 17 alone, or on a portion of just one of the lobes 16, 17 and on a portion of C-shaped end 12. This is because the eye protector 2 may be secured to a user's eye with adhesive located at one end 12, 14 only. It will be further appreciated that adhesive need not be used to retain the overlap of lobes 16, 17. Rather, other methods known to those skilled in the art, such as for example and without limitation one or more interlocking slit(s) formed in one or both lobes 16, 17 may be used. In any event, the adhesive may have the same transmittance properties as the film itself and/or may add to the transmittance properties of the film 10.

The composition of film member 10 is not critical so long as its mechanical, spectral transmittance and other physical properties are such that it will afford the desired eye protection. For example, if the eye protector is intended to protect the eye against eye irritants, such as those which may be encountered in certain hair treatments, film member 10 should be liquid impervious. Further, film member 10 could be opaque, transparent or translucent. However, since users of protective eyewear may prefer to "see" while the protective eyewear is in place and covering the eyes, it may be desirable to form film member 10 from a polymeric film which is transparent to at least a portion of incident visible radiation.

Where the protective eyewear is used to reduce the exposure of an eye to ultraviolet radiation, shaped film member 10 illustratively should be formed from a film comprising an ultraviolet light absorbing polymer. Illustratively, film member 10 should be essentially opaque to ultraviolet light according to applicable regulations as desired. For example and without limitation, U.S. federal regulations specify that protective eyewear for use with UV emitting sunlamp products have a radiation transmittance of less than about 0.001 for radiation having a wavelength ranging from about 200 to about 320 nanometers and a transmittance value less than about 0.01 for radiation having a wavelength ranging from about 320 nanometers to about 360 nanometers. In another example, EN 170:2002 specifies that eye protectors used in conjunction with high-pressure mercury lamps and metal halide lamps such as sun lamps for solaria have a maximum spectral transmittance ($\tau(\lambda)$) of less than about 0.0003% in the range 210–313 nanometers, is 2% in the range 313–365 nanometers, and is less than the luminous transmittance ($\tau_v$) in the range 365–405 nanometers, wherein the luminous transmittance is between a minimum of 8.5% and a maximum of 17.8%.

Polymeric films suitable for use in accordance with the present invention are well known in the art and readily available commercially either as monolayer films or multilayer film laminates. Thus, CW-shaped film member 10 can be formed from a polymeric film selected from acrylic polymers, for example and without limitation, acrylate, methacrylate and copolymers thereof; polyethylene and copolymers of ethylene and other olefin monomers such as hexene-1 and butene-1; polypropylene; polyvinylchloride and copolymers thereof; nylon; and polyesters, for example and without limitation, polyethylene terephthalate. Such polymeric films are well known in the art and are commercially available in thicknesses ranging from less than about 0.5 mils to more than about 10 mils (1 mil equals 0.001 inch). These examples are not meant to be limiting, however, and other materials may be used.

The optical properties and other physical properties of the illustrative eyewear or eye protector are determined by the thickness and composition of the polymeric materials used for forming the CW-shaped film member 10. For example, light transmittance of the eye protector can be produced by utilizing a vacuum metallized polymeric film, usually a biaxially oriented polymeric film, to form CW-shaped film member 10. In one embodiment, CW-shaped film member 10 is formed from a laminate of two or more polymeric films, at least one of which is a metallized biaxially oriented polyethylene terephthalate. Such metallized film laminates are well known in the art and have found utility as solar control film and as packaging material for various foods. The second polymeric film layer in such art-recognized laminates is typically a polyester or a polyolefin such as polyethylene. In another embodiment of this invention, CW-shaped film member 10 is formed from a laminate of two or more polymeric films, at least one of which is a clear laminate layer and having at least one laminate layer incorporating a UV-absorbing material.

Some polymers, for example those containing aromatic ring structures and other UV absorbing functional groups, strongly absorb UV radiation and inherently have low UV transmittance. Other types of polymeric films do not inherently have such UV absorbing polymeric groups but can be modified by including art-recognized UV absorbing "stabilizers" during the polymer film formation process.

Commonly used UV absorbing or stabilizing compounds are substituted benzophenone and substituted benzotriazole compounds. The most common benzophenone compounds used as UV stabilizers for polymeric films are for example and without limitation 2,4-dihydroxy-benzophenone, 2-hydroxy-4acryloxyethoxybenzophenone, 2-hydroxy-4-methoxy-benzophenone, 2,2'-dihydroxy-4methoxy-benzophenone, 2,2'-dihydroxy-4,4'dimethoxy-benzophenone, 2-hydroxy-4-noctoxybenzophenone, 2,2',4,4'-tetrahydroxy-benzophenone, and 4-dodecyloxy-2-hydroxybenzophenone. Most common of the substituted benzotriazoles used as UV stabilizers in polymeric films are for example and without limitation 2(2'-hydroxy-5'-methylphenyl)benzotriazole, 2-(3,3',5'-di-t-butyl-2'hydroxyphenyl)-5-chlorobenzotriazole, 2-(3'-t-butyl-2'-hydroxy-5'-methylphenyl)-5chlorobenzotriazole, 2(2'-hydroxy-3',5'-di-t-butylphenyl)benzotriazole, 2(2'-hydroxy-3',5'-di-t-amylphenyl)benzotriazole, and 2-(2'-hydroxy-5-t-octylphenyl)benzotriazole. Addition of such UV stabilizers to polymeric films not only reduces UV light-induced degradation of those films in the long term, but also reduces film transmittance of UV light. Polymeric films formulated using such ultraviolet stabilizers are well known in the art, as are laminates of such UV stabilized film with, for example, metallized biaxially oriented polymeric film.

Illustratively, the transmittance properties of the film laminates can also be controlled to some extent by the nature and components of the laminating adhesive used to adhere the component films forming the film laminate. Thus, UV absorbance of a film segment in accordance with this invention can be minimized by forming the segment from a film laminate using polymeric films which (1) inherently have UV absorbing functional groups, (2) which have been UV stabilized by the use of art-recognized UV stabilizers and (3) which have been laminated using adhesives comprising compounds having UV absorbing functional groups.

Illustratively, the desired film(s) may be treated or coated on a side with a chemical adhesion promoter and laminated together with a transmittance controlling laminating adhesive, the dermal adhesive may be applied to the treated side and the laminated film applied to the web, carrier or release liner 28. The carrier or liner may be for example a silicone coated release liner. The film may be die cut to the desired shape and printed with any letters or colors. The films and adhesive may be chosen to allow the desired transmittance values. For example, such transmittance values may range from about 0.0001% to about 0.04% for radiation having a wavelength from about 200 to about 320; from less than about 0.01% to about 0.1% for radiation having a wavelength from about 320 to about 360 nanometers, and from about 0.9% to about 18.0% for radiation having a wavelength from about 360–405 nanometers.

For example, in one illustrative embodiment, the film segment has a transmittance value of less than about 0.001 for radiation having a wavelength from about 200 to about 320 nanometers and a transmittance value of less than about 0.01 for radiation having a wavelength ranging from about 320 to about 360 nanometers while at the same time being transparent to at least a portion of incident visible radiation. The CW-shaped film segment is formed from a partially transparent film laminate comprising a biaxially oriented metallized polyethyleneterephthalate film and a medium to low density UV stabilized polyethylene or polyester film. Preferably, the thickness of the film laminate is between about 2 mils and about 8 mils. In another embodiment, the film segment had a transmittance value of about 0.0001% for radiation having a wavelength ranging from about 200 to about 320 nanometers and of about 0.06% for radiation having a wavelength ranging from about 320 to about 360 nanometers. In another illustrative embodiment, testing of two film segments 10 according to EN 170:2002 clause 5.2 revealed a transmittance level ($\tau(\lambda)$) of less than or equal to about 0.0003% in the range 210–313 nanometers for each sample, of less than about 0.1% in the range 313–365 nanometers for each sample, and of about 11.85% for sample 1 and about 13.39% for sample 2 in the range 365–405 nanometers. The spectral transmittances were measured for the range 210–780 nanometers over an area 5 mm in diameter. During another test an embodiment had a transmittance level of less than or equal to about 0.0002% in the range 210–313 nanometers, of less than about 0.034% in the range 313–365 nanometers, and of about 2.8% in the range 365–405 nanometers. In still another test, a sample tested at about 0.04% in the range 200–320 nanometers, at about 0.04% in the range 320–400 nanometers, and at about 3.00% for the range 400–700 nanometers.

Figure 7:
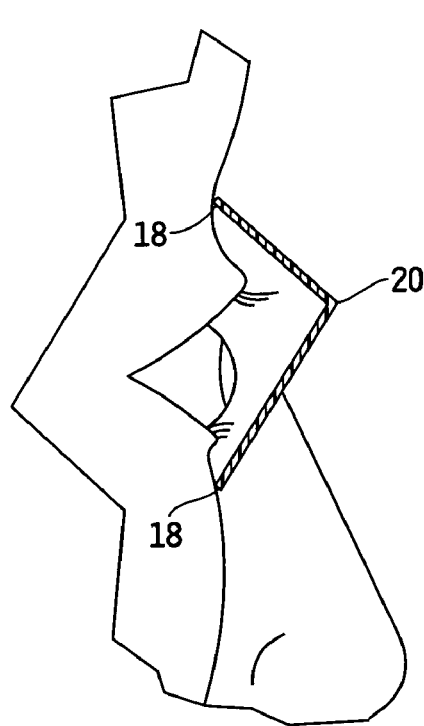
FIG. 7 is a lateral cross-sectional view taken generally along the line 7—7 of the illustrative eye protector of FIG. 6 positioned over a user's eye.
Figure 8:
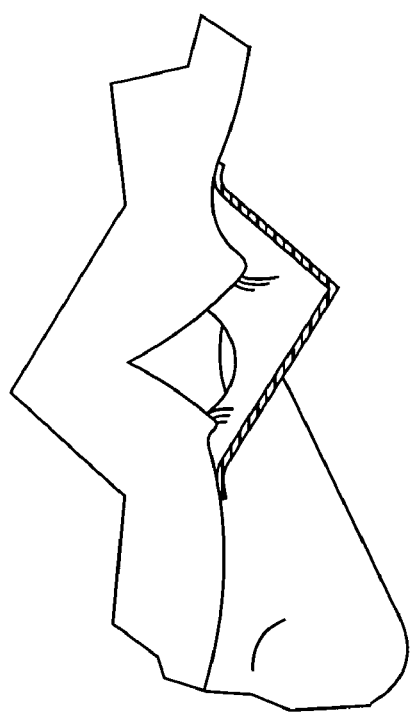
FIG. 8 is a lateral cross-sectional view of prior art eyewear.

Illustratively, adhesive 30 is disposed along at least one lobe 16 or 17 on eye proximal side 4. This configuration allows film member 10 to be fashioned into a conical shape as described earlier, However, in an illustrative embodiment, adhesive 30 is disposed on both lobes 16 and 17 on eye proximal side 4. This positioning of adhesive 30 allows film member 10 to be formed into a conical shape by using the adhesive of one lobe (16 or 17) to retain the film member in a conical shape while the adhesive of the other lobe (16 or 17) remains free to be used for bonding to a user's eye. As also noted above, and as depicted in FIG. 3, adhesive 30 may also be disposed within a distal portion of C-shaped end 12. This adhesive on C-shaped portion 12 could be used either alone to retain the eye protector 2 on a user thus eliminating the need for adhesive 30 to be disposed on both lobes 16 and 17; or, it could be used in conjunction with the adhesive on the lobe not being used to form the conical shape. After conical formation, eyewear 2 includes a first and second end 22 and 24, respectively, with adhesive 30 disposed thereon (FIG. 4). This placement of adhesive 30 along the major axis allows the eyewear to be adhered to the user at the sides of the user's eye rather than above and below the eye as in prior art eye protectors or eyewear. Among other advantages, this positioning of adhesive 30, toward the side of the user's eye, allows the eyewear to be used without interfering with a user's makeup. For example, by positioning adhesive 30 at the side of the eye, eye-shadow will not be removed or smudged as it would be if the adhesive was disposed on the top and bottom of the eyepiece as it is in the prior art (FIG. 8). This is due to the prior art adhesive adhering over the eyelid where eye-shadow is used (FIG. 8). As seen in FIGS. 4 and 5, the lobes overlap to form the apex 20 of the cone in an asymmetrical manner. Illustratively, therefore, as best seen in FIGS. 6 and 7, the eye protector is placed over the eye with the apex 20 displaced to one side or the other of the pupil. Additionally, to secure the eyewear, at least a slight pressure is needed to adhere the adhesive to the skin resulting in the makeup being smudged. However, when the adhesive is located to the side, the amount of adhesive which touches an area where eye-shadow is used is significantly, if not completely, reduced.

The nature of adhesive 30 utilized in accordance with the present invention can be varied. Many synthetic, acrylic, pressure sensitive and natural rubber based adhesives are known in the art. Illustratively, adhesive 30 is a non-allergenic, medical grade adhesive such as those which have been used on medical tapes and dressings. Such adhesives are commonly available, for example, in the form of a transfer tape with a release liner. Thus, in one illustrative embodiment, the shape of film member 10 can be cut from a sheet of polymeric film or film laminate on which a transfer tape has been applied in a predetermined pattern so that the die cut film members 10 each have the desired positioning of applied adhesive 30 (FIG. 9).

In another embodiment, a method of manufacturing and/or merchandising disposable protective eyewear is disclosed and includes providing an adhesive on a carrier or web 28 as shown in FIG. 9, wherein the adhesive 30 illustratively is disposed along at least one edge and a center portion of the carrier or web. A layer of disposable protective-eyewear material 10 is positioned over the carrier web and adhered. The disposable protective eyewear material is then cut into a desired shape which includes a portion of the center and at least one edge of adhesive. This creates a plurality of eye protectors 2, wherein the adhesive 30 is disposed on a first C-shaped end and a second W-shaped end such that, each film member or eye protector 2 can be peeled off of the carrier 28 and after manipulation into a conical shape, the eye protector 2 may be adhered to the user's eye along sides thereof. This method of merchandising allows the eyewear to be manufactured in an efficient manner and then sold on the same carrier web as used in the manufacturing process. This allows the eyewear to be distributed in either roll form or sheet form, thereby providing an efficient and inexpensive distribution method. This allows the manufacturing and distribution costs of the eyewear to be kept to a minimum. In another embodiment, the eye protectors 2 may be cut from the film 10 and disposed on the carrier 28. Additionally, other shapes 40 may be cut into either the edge or center adhesive material, as for example, tanning decals as described below.

In still another embodiment, the method of merchandising further includes providing a plurality tanning decals 40 on the same carrier as the protective eyewear as disclosed above. Tanning decals are decals which are used to prevent the tanning of the skin in an area under the decal. This in turn leaves an image, or more appropriately the lack of an image, on the skin where the decal was disposed. These decals may be formed from the same ultraviolet reducing films as described with respect to the protective eyewear and are formed into various shapes. These shapes define the "image" that is then left on the skin.

In use, these decals are removed from the carrier and positioned, on a user's body in any desired location. When the user is exposed to UV light, such as at a tanning salon, the area covered by the decals will block most of the UV light thereby not allowing the area under the decal to be tanned, while the rest of the surrounding area is not prevented from receiving the UV light and will be tanned or change color in response to the UV light. For example, the heart shape 40 decal of FIG. 9 will leave a heart-shaped image on the skin of the user. This image may be used, for example, to indicate the degree of tanning attained while wearing the decal because the area around the decal will not be impeded from tanning in contrast to the skin under the decal. In this embodiment, these decals illustratively are disposed on the same carrier 28 and alongside the protective eyewear. This allows the decals 40 and eyewear 2 to be marketed and used together such that a user of the eyewear is also provided with the tanning decals. Therefore, this method of packaging and marketing increases-the desirability of the eyewear by offering the customer the added feature of a tanning decal at little to no cost increase to the manufacturer.

In another embodiment, the back of the carrier 28 may be provided with instructions for the proper use of the eye protectors 2. In one illustrative embodiment, the instructions may direct the user to cross the lobes 16 and 17 over one another such that when they are properly adhered together they form a recognizable shape, for example and without limitation a heart 29. As shown in FIG. 6, however, the overlapping separated portions 16 and 17 need not form the heart. Illustratively, the lobes 16 and 17 may be of a different color than at least the rest of the film contiguous to the separated lobes, namely, the rest of the film on the eye distal second side contiguous to the lobes. The different color, among other things, may help to better provide a visual depiction of the heart 29 or other recognizable shape or pattern as an indication to the user of correct formation. For example and without limitation the separated portions or lobes 16, and 17 may be a red or purple color while the rest of the eye protector is gold. Illustratively the eye distal second side may be the one with the purple and gold color, or any other color or combinations of colors; while the eye proximal first side may be identical to the second side or may be a uniform color, which uniform color may even be a color, such as for example silver, not found on the second side at all. One skilled in the art could also appreciate that fanciful designs or even operating instructions may be printed or otherwise disposed directly on the film 10.

The embodiments described above provide disposable protective eyewear which may be utilized to protect a user's eyes from various light sources as well as certain physical contaminants. Illustratively, the disposable protective eyewear pieces may be manufactured via an inexpensive manufacturing process on a carrier 28 and then formed into conical disposable eye protection. The carrier 28 may have one row, two rows, or more than two rows of eye protectors 2 disposed on the carrier 28, which may be a flat sheet, or may be rolled. Decals 40 may also be disposed on the carrier. In the example of a carrier containing two rows of eye protectors 2, the carrier 28 illustratively may be about 4.5625 inches wide, and may have scored panels containing each of the opposing pairs of eye protectors 2 and corresponding pair of decals 40 that are about 1.5 inches wide from score 33 to score 33 along the length of the carrier 28. Thus, a panel of the carrier having a pair of eye protectors 2 and a pair of decals and measuring about 4.5625 inches by about 1.5 inches may be torn off from the rest of the carrier 28 for use by a user. Instructions, including color-coded shapes to indicate proper formation, may be provided on the carrier 28, or even on the eye protector itself. The eye protectors or pieces are then adhered to the user's eye perimeter, along sides thereof, creating inexpensive disposable protective eyewear which allows the user to see through while simultaneously not interfering with the user's ability to blink or the user's makeup, if so used.

Of course, it is to be understood that the foregoing are preferred embodiments and changes and variations can be made without departing from the spirit and broader aspects of the invention, as defined in the appended claims, which are interpreted in accordance with the principles of patent law, including the Doctrine of Equivalents.

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected.

What is claimed is:

1. Protective eyewear comprising:
    a flexible film that can be shaped into an oblong conical configuration so that it can be fitted over a user's eye;
    the base of the oblong conical configuration having a major axis and a shorter minor axis;
    the film including an adhesive disposed on one side thereof, located generally at the ends of said major axis;
    the film being free of adhesive at the ends of said minor axis;
    wherein when said film in its oblong conical configuration is positioned over the user's eye with its major axis corresponding to the major axis of the user's eye, the adhesive is located at least at one of the two ends of the eye rather than at the top or bottom of the user's eye.

2. The eyewear of claim 1, in which:
    said film is made of a material which reduces the transmission of ultraviolet light through said film.

3. The eyewear of claim 2, wherein the film reduces transmission of ultraviolet light through the film in compliance with at least a portion of applicable local, state or federal regulations, rules or laws.

4. The eyewear of claim 3 wherein one applicable regulation comprises EN 170:2002.

5. The eyewear of claim 1, in which:
    said film is separated at one end of said major axis such that it can be formed into said oblong conical configuration by overlapping separated portions of said film and using a portion of the adhesive located at said one end of said major axis to hold the overlapping portions of said film together.

6. The eyewear of claim 5, in which:
    said film is generally C-shaped in configuration at one end of said major axis and is generally W-shaped at the other of said major axis, said separation in said film being formed by the space between the two halves of said W.

7. The eyewear of claim 6, in which:
    said adhesive at said separated end of said longitudinal axis is located on said two halves of said "W."

8. The eyewear of claim 5, in which:
    said separation in said film begins at one end of said longitudinal axis and extends generally along the length of said longitudinal axis for a distance sufficient to facilitate forming said film into said cone shape, but short of the center of said longitudinal axis, whereby the apex of said cone is formed to one side of the center of said longitudinal axis and is thereby out of the direct forward line of sight of the user.

9. The eyewear of claim 8, in which:
    said separation is defined by said film being a generally "W" shaped configuration at said one end of said longitudinal axis, said separation occurring between the two halves of the "W."

10. The eyewear of claim 9, in which:
    said separation is further defined by a slit in said film, extending generally along said longitudinal axis from the point at which the two halves of said "W" meet.

11. The eyewear of claim 10, in which:
    said adhesive at said separated end of said longitudinal axis is located on said two halves of said "W."

12. The eyewear of claim 9, in which:
    said adhesive at said separated end of said longitudinal axis is located on said two halves of said "W."

13. The eyewear of claim 9, in which:
    said film is made of a material which reduces the transmission of ultraviolet light through said film.

14. The eyewear of claim 8, in which:
    said film is made of a material which reduces the transmission of ultraviolet light through said film.

15. The eyewear of claim 5, wherein when the separated portions are overlapped they form a recognizable shape.

16. The eyewear of claim 15, wherein the formation of the recognizable shape indicates to the user the proper formation of the conical configuration.

17. The eyewear of claim 15, wherein the recognizable shape comprises a heart.

18. The eyewear of claim 5, wherein the separated portions are a different color from at least a portion of the rest of the flexible film.

19. The eyewear of claim 1, wherein the radiation transmittance of the film is less than about 0.001 for radiation having a wavelength ranging from about 200 to about 320 nanometers and a value less than about 0.01 for radiation having a wavelength ranging from about 320 nanometers to about 360 nanometers.

20. The eyewear of claim 19, wherein the film further comprises a UV absorbing polymeric film having a visible light transmittance of greater than about 0.9.

21. The eyewear of claim 1, wherein the radiation transmittance of the film is less than about 0.0003% for radiation having a wavelength ranging from about 210 to about 313 nanometers and a value less than about 2.0% for-radiation-having a wavelength ranging from about 313 nanometers to about 365 nanometers.

22. A method for reducing the exposure of an eye to eye irritants and ultraviolet radiation, comprising the steps of:
    providing a film that can be shaped into a generally oblong conical configuration so that it can be fitted over a user's eye, the base of said oblong conical configuration having a major axis and a shorter minor axis, said film including an adhesive disposed on at least one side thereof, located generally at the ends of said major axis, said film being free of adhesive at the ends of said minor axis;
    forming said film into a generally oblong conical configuration;
    positioning said film over the user's eye with its major axis corresponding to the major axis of the user's eye; and
    adhering said oblong conical configuration to at least one end of the user's eye rather than the top or the bottom of the user's eye.

23. The method of claim 22, in which:
    said provided film is made of a material which reduces the transmission of ultraviolet light through said film.

24. The method of claim 22, in which:
    said provided film is separated at one end of said major axis such that it can be formed into said oblong conical configuration by overlapping separated portions of said film and using a portion of the adhesive located at said one end of said major axis to hold the overlapping portions of said film together.

25. The method of claim 24, in which:
    said provided film is generally C-shaped in configuration at one end of said major axis and is generally W-shaped at the other end of said major axis, said separation in said film being formed by the space between the two "V's" of said W.

26. A method of manufacturing disposable protective eyewear comprising the steps of:
    providing a carrier web;

adhering an adhesive to said carrier web, said adhesive being disposed along at least one edge and a center portion of said carrier web;

positioning a layer of a film material sufficiently flexible that it can be shaped into an oblong conical configuration so that it can be fitted over a user's eye;

adhering said film material to said adhesive on said carrier; and cutting said film material to a first desired shape such that it can be further shaped into an oblong conical configuration, the base of said oblong conical configuration having a major axis and a shorter minor axis, said shape including a portion of said center portion and said at least one edge of said adhesive on said carrier.

27. The method according to claim 26, wherein the first desired shape includes opposing C-shaped and W-shaped ends along said major axis.

28. The method according to claim 27, wherein the adhesive is disposed on said C-shaped end and said W-shaped end, said film being free of adhesive at the ends of said minor axis.

29. The method according to claim 27, wherein said disposable protective eyewear further includes a slit disposed between a first and a second lobe of said W-shaped end.

30. The method according to claim 26, wherein a second desired shape is cut into said film material in the at least one edge or the center portion of said adhesive which is not cut for said first desired shape.

31. The method according to claim 26, wherein the first desired shape includes opposing C-shaped and W-shaped ends along said major axis.

32. A method of merchandising disposable protective eyewear comprising the steps of:
   providing a plurality of protective eyewear film pieces, said film pieces disposed on a carrier; and
   providing at least one tanning decal disposed on said carrier alongside said disposable protective eyewear.

33. The method of merchandising disposable protective eyewear of claim 32, wherein said film pieces are sufficiently flexible so that it can be shaped into an oblong conical configuration which can be fitted over a user's eye, the base of said oblong conical configuration having a major axis and a shorter minor axis; wherein when said film pieces are removed from said carrier, said film pieces include an adhesive disposed on one side thereof located generally at the ends of said major axis, said film being free of adhesive at the ends of said minor axis.

34. The method of merchandising disposable protective eyewear of claim 32, wherein said carrier is a silicone coated release liner.

35. The method of merchandising disposable protective eyewear of claim 33, wherein said tanning decal is heart-shaped.

36. The method of merchandising disposable protective eyewear of claim 33, wherein the disposable protective eyewear piece includes opposing laterally C-shaped and W-shaped ends.

37. The method of merchandising disposable protective eyewear of claim 36, wherein said disposable protective eyewear further includes a longitudinal slit disposed between a first and second lobe of said W-shaped end.

38. Protective eyewear comprising:
   a flexible film comprising an elongated generally C-shaped portion opposite a generally W-shaped portion, the W-shaped portion having separated portions that can be overlapped and adhered to one another in order to form an asymmetrical conical configuration that can be fitted over a user's eye;
   the base of the asymmetrical conical configuration having a major axis and a shorter minor axis;
   the film including an adhesive disposed on one side thereof, located generally at the ends of said major axis;
   whereby when said film in its asymmetrical conical configuration is positioned over the user's eye with its major axis corresponding to the major axis of the user's eye, the adhesive is located at least at one of the two ends of the eye.

39. The protective eyewear of claim 38, further comprising a scission line extending radially inwardly from a point where the separated portions generally meet toward the center of the film.

40. The protective eyewear of claim 39, wherein when the separated portions are properly overlapped, they form a recognizable shape.

* * * * *